United States Patent [19]

Weigert

[11] Patent Number: 4,763,075
[45] Date of Patent: Aug. 9, 1988

[54] ELECTRO-OPTICAL ISOLATOR FOR MAGNETIC RESONANCE TOMOGRAPHY

[75] Inventor: Kurt Weigert, Fuerth, Fed. Rep. of Germany

[73] Assignee: Siemens Aktiengesellschaft, Berlin and Munich, Fed. Rep. of Germany

[21] Appl. No.: 756,883

[22] Filed: Jul. 19, 1985

[30] Foreign Application Priority Data

Aug. 20, 1984 [DE] Fed. Rep. of Germany ....... 3430625

[51] Int. Cl.⁴ ........................................... G01R 33/20
[52] U.S. Cl. ..................................... 324/318; 324/322
[58] Field of Search ............... 324/318, 300, 307, 309, 324/314, 304, 305, 322, 95, 96, 72; 128/653, 696, 709, 716; 378/95; 455/602, 612; 250/551

[56] References Cited

U.S. PATENT DOCUMENTS

| | | | |
|---|---|---|---|
| 3,564,398 | 2/1971 | Nelson | 324/320 |
| 4,290,146 | 9/1981 | Adolfsson et al. | 324/96 |
| 4,387,722 | 6/1983 | Kearns | 378/95 X |
| 4,413,233 | 11/1983 | Fossel et al. | 324/309 |
| 4,537,200 | 8/1985 | Widrow | 128/696 |
| 4,539,999 | 9/1985 | Mans | 128/696 |
| 4,564,017 | 1/1986 | Glover | 128/653 |
| 4,564,812 | 1/1986 | Van Dijk | 324/318 |
| 4,567,893 | 2/1986 | Charles et al. | 128/653 |
| 4,602,641 | 7/1986 | Feinberg | 324/309 X |

FOREIGN PATENT DOCUMENTS

| | | |
|---|---|---|
| 0098426 | 1/1984 | European Pat. Off. . |
| 0105550 | 4/1984 | European Pat. Off. . |
| 3216273 | 11/1983 | Fed. Rep. of Germany ...... 128/653 |
| 2126731 | 3/1984 | United Kingdom . |

OTHER PUBLICATIONS

T. J. Pratt et al., Optical Tachometry for Monitoring Nuclear Magnetic Resonance Sample Spinning Rates, J. Phys. E., vol. 3, Dec., 1970.

General Electric, NMR, Site Planning Considerations, published by the Medical Systems Operations.

*Primary Examiner*—Michael J. Tokar
*Attorney, Agent, or Firm*—Mark H. Jay

[57] ABSTRACT

The invention relates to equipment for magnetic resonance tomography where, for the formation of physiological test signals, an electronic measuring system with an electro-optical transducer is arranged in a shielded cabin receiving the magnetic resonance tomograph. From this transducer a beam waveguide leads to an electronic processor with an opto-electric transducer provided outside the cabin. At the input, the electronic measuring system comprises a radio-frequency filter, a following wideband amplifier and thereafter, before the electro-optical transducer, a slew rate filter.

3 Claims, 2 Drawing Sheets

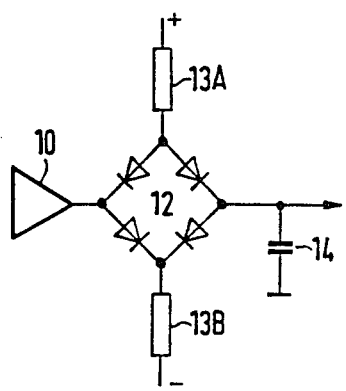
FIG 2
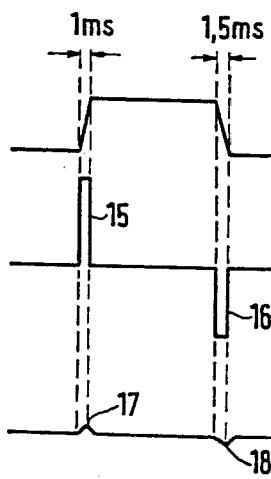
FIG 3
FIG 4
FIG 5

ELECTRO-OPTICAL ISOLATOR FOR MAGNETIC RESONANCE TOMOGRAPHY

BACKGROUND OF THE INVENTION

The invention relates to magnetic resonance (MR) tomography. This produces a pictorial representation of partial regions from the interior of a test object using coils for applying magnetic primary and gradient fields to the test object and an antenna for picking up the deflection of the nuclear spins of the test object from their equilibrium position by radio-frequency magnetic excitation pulses.

A device of this kind is described in U.S. Pat. No. 3,564,398. This device is suitable for deflecting the hydrogen atom nuclei of the test object and to detect their swinging back into equilibrium. Based on the measured signals, the proton distribution of a certain stratum of the test object can be represented pictorially.

In a device of this kind the problem arises that for the observation of moving body regions a triggering (or gating) of the imaging process must occur as a function of the respiration and/or the heartbeat (EKG) of the patient. To this end a respiration detector and EKG electrodes may be provided which generate electrical signals depending on the respiration and on the cardiac activity, which signals cause the gating of the imaging process.

One object of the invention is to develop a device of the initially mentioned kind so that there are formed disturbance-free physiological test signals, which in particular depend on respiration and on the EKG, and which permit a satisfactory gating of the imaging process.

SUMMARY OF THE INVENTION

According to the invention, there is arranged in the shielded cabin receiving the device an electronic measuring system. The system has an electric-optical transducer whence a beam waveguide leads to an electronic processor with an opto-electrical transducer, provided outside the cabin. According to the invention, the physiological test signals (processed in suitable manner by the electronic measuring system) are relayed optically, so that in particular the switching of the gradients has no disturbing effect on these test signals.

An especially disturbance-free signal transmission, and which itself causes no interference, results if the electric-optical transducer brings about an analog light modulation.

BRIEF DESCRIPTION OF THE DRAWINGS

Exemplary and non-limiting preferred embodiments of the invention are shown in the drawings, in which:

FIG. 2 shows a detail of the equipment in FIG. 1; and

FIG. 3 to 5, curves to explain the equipment illustrated in FIGS. 1 and 2.

DETAILED DESCRIPTION OF PREFERRED EMBODIMENTS

Figure 1:
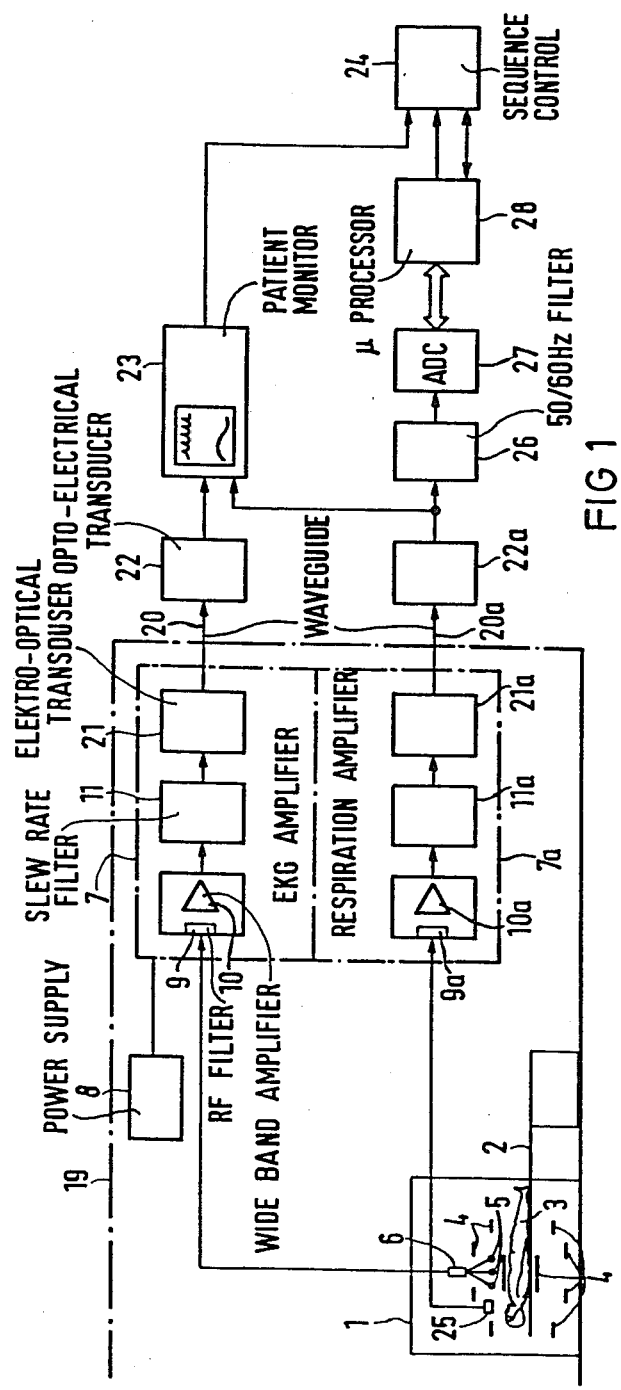
FIG. 1 shows an MR spin tomograph which uses the invention.

In FIG. 1 is shown a nuclear spin tomograph 1 comprising a stretcher 2 with a patient 3 lying on it. For the examination of the patient 3 the MR tomograph 1 comprises a schematically shown coil arrangement 4 for applying magnetic primary and gradient fields to the test object; the coil arrangement 4 has an antenna for picking up the deflection of the nuclear spins of the test object from their equilibrium position by radio-frequency magnetic excitation pulses. The test signals are processed in known manner to form a picture of a stratum of the patient 3.

To trigger the data generation as a function of the patient's EKG, there are assigned to the patient 3 e.g. EKG electrodes 5, which are connected to an EKG amplifier 7 via resistors 6. The EKG amplifier 7 is supplied by a power supply unit 8 and comprises at its input a radio-frequency filter 9 and following it a wide-band amplifier stage 10 with a passband between 0.1 and 10 kHz, for example. The gain of the amplifier stage 10 is selected so that the interference pulses generated by the gradient pulses still lie within the linear operating range of the amplifier stage 10, i.e. that the amplifier stage 10 is not overmodulated. At the output of the amplifier stage 10 is a slew rate filter 11. By the slew rate filter 11 the interfering pulses generated with the rise and decay of the gradient pulses (FIG. 3) are effectively suppressed.

The construction of the slew rate filter 11 is illustrated more specifically in FIG. 2. The figure shows that the slew rate filter 11 comprises a rectifier bridge 12 which, via two like resistors 13A and 13B is connected respectively to the positive and negative poles of a d-c voltage source (not shown). At the output of the slew rate filter 11 a capacitor 14 is connected.

The gradient pulses according to FIG. 3 have rise and decay times of 1 ms and 1.5 ms, respectively. During this rise or decay, the signal (as shown in FIG. 4) contains interference pulses 15, 16 before the slew rate filter 11. After the slew rate filter 11, these interference pulses 15, 16 cause, according to FIG. 5, residual interference pulses 17, 18, whose amplitude depends only on the pulse width (FIG. 4) and not on the amplitude of the pulses 15, 16. Accordingly, the slew rate filter 11 effectively suppresses the interference pulses generated during the rise and decay of the gradient pulses.

The output signal of the slew rate filter 11 is relayed from the shielded cabin 19 receiving the nuclear spin tomograph 1 via a beam waveguide 20 which is preceded by an electro-optical transducer 21. The transmission takes place by analog modulation of the light, so that interferences continue to be reduced. Outside cabin 19 an opto-electric transducer 22 is provided, which supplies the EKG signal to a patient monitor 23. The measuring process can be triggered by monitor 23 via a sequence control 24 as a function of the EKG.

The series resistors 6 are chosen to minimize the influence of the electrodes on the image as well as the relay of the radio frequency via the electrode lines or respectively the current induced by the radio frequency in the electrode lines.

A similar signal transmission takes place for the the breath signal generated by a respiration detector 25. The components corresponding to the components 9, 10, 11, 20, 21 and 22 are marked 9a, 10a, 11a, 20a, 21a and 22a. The opto-electric transducer 22a brings about a reproduction of the respiration curve on the patient monitor 23 and controls the sequence control 24 via a 50/60 Hz filter 26, an analog/digital converter 27, and a microcomputer 28.

Those skilled in the art will understand that changes can be made in the preferred embodiments here described, and that these embodiments can be used for other purposes. Such changes and uses are within the scope of the invention, which is limited only by the claims which follow.

What is claimed is:

1. Apparatus for use with magnetic resonance tomography equipment to gate the imaging process without excessive electrical interference from gradient pulses and like electrical signals, wherein at least a part of said magnetic resonance tomography equipment is located inside a shielded region, comprising:

an electronic measuring system located inside said region and responding to a one of a patient's body functions to produce an electrical signal suitable for gating, said system comprising a slew rate filter;

an electro-optical transducer located inside said region and converting said electrical signal to an optical signal;

as waveguide coupled to the electro-optical transducer and transmitting said optical signal outside said region; and an opto-electrical transducer located outside said region and coupled to said waveguide, said opto-electrical transducer converting said optical signal to an electrical output signal.

2. The apparatus of claim 1, wherein the electro-optical transducer produces an analog optical signal.

3. The apparatus of claim 1, wherein the electronic measuring system further comprises an RF-filter at its input and a wideband amplifier connected to the RF-filter, and the slew rate filter is connected between the wideband amplifier and the electro-optical transducer.

* * * * *